(12) United States Patent
Fink

(10) Patent No.: US 7,110,110 B2
(45) Date of Patent: Sep. 19, 2006

(54) SENSING COMPONENT USED TO MONITOR MATERIAL BUILDUP AND MATERIAL EROSION OF CONSUMABLES BY OPTICAL EMISSION

(75) Inventor: Steven T. Fink, Mesa, AZ (US)

(73) Assignee: Tokyo Electron Limited, Tokyo (JP)

( * ) Notice: Subject to any disclaimer, the term of this patent is extended or adjusted under 35 U.S.C. 154(b) by 108 days.

(21) Appl. No.: 10/745,577

(22) Filed: Dec. 29, 2003

(65) Prior Publication Data
US 2005/0213079 A1 Sep. 29, 2005

(51) Int. Cl.
*G01J 3/30* (2006.01)
(52) U.S. Cl. ...................................... 356/316
(58) Field of Classification Search ................. 356/316
See application file for complete search history.

(56) References Cited

U.S. PATENT DOCUMENTS

| 5,146,098 A | * | 9/1992 | Stack ...................... 250/492.2 |
| 5,187,542 A | * | 2/1993 | Madzsar ...................... 356/300 |
| 5,712,702 A | * | 1/1998 | McGahay et al. ........... 356/326 |
| 5,798,016 A | * | 8/1998 | Oehrlein et al. .............. 216/67 |
| 5,947,053 A | | 9/1999 | Burnham et al. |
| 2002/0149001 A1 | * | 10/2002 | Ellens et al. ........... 252/301.4 S |

* cited by examiner

*Primary Examiner*—Gregory J. Toatley, Jr.
*Assistant Examiner*—Kara Geisel
(74) *Attorney, Agent, or Firm*—Oblon, Spivak, McClelland, Maier & Neustadt, P.C.

(57) ABSTRACT

A sensing device for sensing a condition of a plasma processing system component. The sensing device includes a main body configured to contain a material, an emitter contained in the main body and configured to emit light when exposed to a plasma, and a mating feature connected to the main body and configured to be mated with a receiving feature of an object in the plasma processing system such that the emitter material is exposed to a processing environment of the plasma processing system. When the emitter material is exposed to a plasma, the light emitted from the emitter can be monitored to determine at least one of material accumulation on the system component and erosion of the system component.

56 Claims, 13 Drawing Sheets

SENSING COMPONENT USED TO MONITOR MATERIAL BUILDUP AND MATERIAL EROSION OF CONSUMABLES BY OPTICAL EMISSION

CROSS REFERENCE TO RELATED APPLICATIONS

The present invention is related to U.S. patent applications Ser. No. 10/331,349 filed on Dec. 31, 2002 and, Ser. No. 10/331,456, also filed on Dec. 31, 2002. The entire contents of each of these applications is incorporated herein by reference.

FIELD OF THE INVENTION

The present invention relates to plasma processing and more particularly to monitoring either material buildup or material erosion on a sensing component added to or placed close to system components in a plasma processing system using an optical monitoring system.

BACKGROUND OF THE INVENTION

The fabrication of integrated circuits (IC) in the semiconductor industry typically employs plasma to create and assist surface chemistry within a plasma reactor necessary to remove material from and deposit material to a substrate. In general, plasma is formed with the plasma reactor under vacuum conditions by heating electrons to energies sufficient to sustain ionizing collisions with a supplied process gas. Moreover, the heated electrons can have energy sufficient to sustain dissociative collisions and, therefore, a specific set of gasses under predetermined conditions (e.g. chamber pressure, gas flow rate, etc.) are chosen to produce a population of charged species and chemically reactive species suitable to the particular process being performed within the chamber (e.g. etching processes where materials are removed from the substrate or deposition where materials are added to the substrate).

Although the formation of a population of charged species (ions, etc.) and chemically reactive species is necessary for performing the function of the plasma processing system (i.e. material etch, material deposition, etc.) at the substrate surface, other component surfaces on the interior of the plasma processing chamber are exposed to the physically and chemically active plasma and, in time, can erode or become coated with deposits. The erosion or coating of exposed components in the plasma processing system can lead to a gradual degradation of the plasma processing performance and ultimately to complete failure of the system.

Various parts of a plasma processing system consist of consumable or replaceable components that are fabricated from silicon, quartz, alumina, carbon, or silicon carbide, for example. Examples of consumable system components include electrodes, shields, rings, baffles and liners. The consumable nature of the replaceable components can require frequent maintenance of the plasma processing system. This frequent maintenance can produce costs associated with plasma processing down-time and new plasma processing chamber components, which can be excessive.

Consumable parts are commonly cleaned or replaced after detrimental processing conditions or process results are observed. The adverse processing conditions can include plasma arcing, particle formation, variations in substrate etch rate, etch selectivity and etch uniformity. Alternatively, consumable parts can be cleaned or replaced according to a predetermined maintenance schedule that can, for example, be based on the number of plasma operating hours. These methods can result in overdue or premature replacement of consumable system components.

SUMMARY OF THE INVENTION

One object of the present invention is to address the above-described and/or other problems in the art of semiconductor processing apparatus.

Another object of the invention is to provide a discreet sensing component that can be placed on or near a semiconductor processing part to facilitate accurate determination of when the processing part should be replaced or cleaned.

These and/or other objects of the present invention may be provided by a sensing device for sensing a condition of a plasma processing system component. The sensing device includes a main body configured to contain a material, an emitter contained in the main body and configured to emit light when exposed to a plasma, and a mating feature connected to the main body and configured to be mated with a receiving feature of an object in the plasma processing system such that the emitter material is exposed to a processing environment of the plasma processing system. When the emitter material is exposed to a plasma, the light emitted from the emitter can be monitored to determine at least one of material accumulation on the system component and erosion of the system component.

In another aspect of the invention, a plasma processing system includes a plasma processing chamber, a plasma source coupled to the plasma processing chamber and configured to create a plasma from a process gas, and a system component coupled to at least one of the plasma processing chamber and the plasma source. A sensing component is mounted on an object in the chamber and includes an emitter capable of light emission when exposed to the plasma. An optical monitoring system is coupled to the plasma processing chamber and configured to monitor light emission from the plasma processing chamber during a process in order to monitor at least one of material accumulation and material erosion of the system component.

In yet another aspect of the invention, a system component assembly for a plasma processing system includes a system component having a receiving feature and configured to be mounted in a processing environment of the plasma processing system, and a sensing component having a mating feature coupled to the receiving feature of the system component and including an emitter configured to emit light when exposed to plasma. The light emission is used to monitor a status of at least one of material accumulation on the system component and erosion of the system component.

In still another aspect of the invention, a method of configuring a semiconductor processing chamber to enable monitoring of at least one of material accumulation on a semiconductor processing part and erosion of the processing part includes obtaining a discreet sensor component containing an emitter configured to emit light when exposed to a plasma. The discreet sensor component is then mounted to at least one of the semiconductor processing part and an object adjacent to the semiconductor processing part.

BRIEF DESCRIPTION OF THE DRAWINGS

The accompanying drawings, which are incorporated in and constitute a part of the specification, embodiments of the invention, and together with the general description given above and the detailed description of the embodiments given below, serve to explain the principles of the invention wherein.

DETAILED DESCRIPTION OF THE INVENTION

Figure 1:
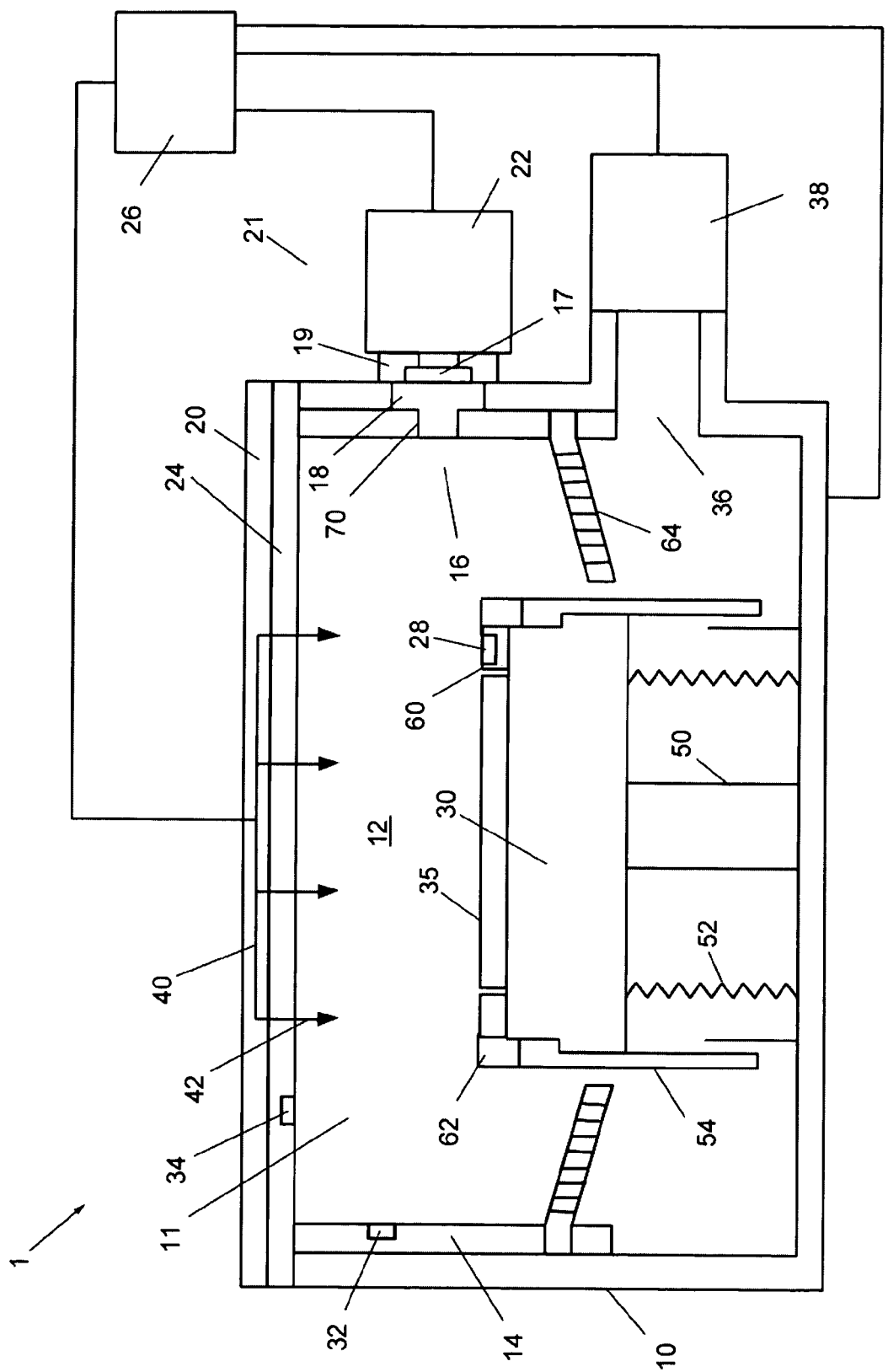
FIG. 1 shows a simplified block diagram of a plasma processing system.

FIG. 1 shows a simplified block diagram of a plasma processing system. A plasma processing system 1 is depicted in FIG. 1 comprising a plasma processing chamber 10, an upper electrode assembly 20, an electrode plate 24, a substrate holder 30 for supporting substrate 35, and pumping duct 36 coupled to a vacuum pump 38 for providing a reduced pressure atmosphere 11 in plasma processing chamber 10. Plasma processing chamber 10 can facilitate the formation of a processing plasma in a process space 12 adjacent to substrate 35. The plasma processing system 1 can be configured to process various substrates (i.e. 200 mm substrates, 300 mm substrates, or larger).

A gas injection assembly 40 can introduce process gas 42 to the plasma processing chamber 10. The gas injection system 40 can include a showerhead (not shown), wherein the process gas 42 is supplied from a gas delivery system (not shown) to the process space 12 through a gas injection plenum (not shown), a series of baffle plates (not shown) and a multi-orifice showerhead gas injection plate (not shown).

For example, an electrode plate 24 can be coupled to an RF source (not shown), and facilitate an upper electrode for the plasma processing system 1. In an alternate embodiment, the upper electrode assembly 20 comprises a cover and an electrode plate 24, wherein the electrode plate 24 is maintained at an electrical potential equivalent to that of the plasma processing chamber 10. For example, the plasma processing chamber 10, the upper electrode assembly 20, and the electrode plate 24 can be electrically connected to ground potential, and facilitate an upper electrode for the plasma processing system 1.

Plasma processing chamber 10 can, for example, further comprise a shield 14 and chamber liners (not shown) for protecting the plasma processing chamber 10 from the processing plasma in the process space 12, and an optical viewport 16. Optical viewport 16 can comprise an optical window 17 coupled to the backside of an optical window deposition shield 18, and an optical window flange 19 can be configured to couple optical window 17 to the optical window deposition shield 18. Sealing members, such as O-rings, can be provided between the optical window flange 19 and the optical window 17 and the optical window deposition shield 18, and between the optical window deposition shield 18 and the plasma processing chamber 10. Optical window deposition shield 18 can extend through an opening 70 within shield 14. Optical monitoring system 21 can permit monitoring of optical emission from the processing plasma in process space 12 using optical viewport 16 and optical diagnostic sensor 22.

A spectrometer (not shown) can be incorporated in the optical diagnostic sensor 22 to detect a plasma process space 12. The spectrometer or the detector system can be associated with a photomultiplier tube, a CCD or other solid state detector to at least partially detect a plasma process condition, such as an endpoint of a plasma process, material buildup on a system component, or status of a system component as examples. However, other optical devices capable of analyzing optical emission, can be used as well.

Substrate holder 30 can, for example, further comprise a vertical translational device 50 surrounded by a bellows 52 coupled to the substrate holder 30 and the plasma processing chamber 10, and configured to seal the vertical translational device from the reduced pressure atmosphere 11 in the plasma processing chamber 10. Additionally, a bellows shield 54 can, for example, be coupled to the substrate holder 30 and configured to protect the bellows 52 from the processing plasma. Substrate holder 30 can, for example, further be coupled to at least one focus ring 60, and shield ring 62. Furthermore, a baffle plate 64 can extend about a periphery of the substrate holder 30.

Substrate 35 can be transferred into and out of plasma processing chamber 10 through a slot valve (not shown) and a chamber feed-through (not shown) via robotic substrate transfer system where it is received by substrate lift pins (not shown) housed within substrate holder and mechanically translated by devices housed therein. Once substrate 35 is received from substrate transfer system, it is lowered to an upper surface of substrate holder 30.

Substrate 35 can be affixed to the substrate holder 30 via an electrostatic clamping system. Furthermore, substrate holder 30 can, for example, include a cooling system including a re-circulating coolant flow that receives heat from substrate holder 30 and transfers heat to a heat exchanger system (not shown), or when heating, transfers heat from the heat exchanger system. Moreover, gas can, for example, be delivered to the backside of substrate 35 via backside gas system to improve the gas-gap thermal conductance between substrate 35 and substrate holder 30. Such a system can be utilized when temperature control of the substrate is required at elevated or reduced temperatures. In other embodiments, heating elements, such as resistive heating elements, or thermoelectric heaters/coolers can be included.

In FIG. 1, substrate holder 30 can comprise an electrode through which RF power is coupled to the processing plasma in process space 12. For example, substrate holder 30 can be electrically biased at a RF voltage via the transmission of RF power from a RF generator (not shown) through an impedance match network (not shown) to substrate holder 30. The RF bias can serve to heat electrons to form and maintain plasma. In this configuration, the system can operate as a reactive ion etch (RIE) reactor, wherein the chamber and upper gas injection electrode serve as ground surfaces. A typical frequency for the RF bias can range from 1 MHz to 100 MHz. For example, plasma processing systems operating at 13.56 MHz are well known to those skilled in the art.

The processing plasma formed in process space 12 can be formed using a plasma source can include a parallel-plate, capacitively coupled plasma (CCP) source, an inductively coupled plasma (ICP) source, any combination thereof, and with and without DC magnet systems. Alternately, the processing plasma in process space 12 can be formed using electron cyclotron resonance (ECR). In yet another embodiment, the processing plasma in process space 12 is formed from launching of a Helicon wave. In yet another embodiment, the processing plasma in process space 12 is formed from a propagating surface wave.

A controller 26 includes a microprocessor, a memory, and a digital I/O port capable of generating control voltages sufficient to communicate and activate inputs to the processing system 1 as well as monitor outputs from the processing system 1. Moreover, the controller 26 is coupled to and can exchange information with the plasma processing chamber 10, the gas injection system 40, optical diagnostic sensor 22 and the vacuum pump system 38. For example, a program stored in memory can be utilized to control the aforementioned components of a plasma processing system 1 according to a stored process recipe. One example of a controller 26 is DELL PRECISION WORKSTATION 610™, available from Dell Corporation, Dallas, Tex.

Various system components can contain or be in close proximity to sensing components, or emitters that are capable of producing characteristic fluorescent light emission to indicate material buildup or material erosion on the sensing components, thereby indicating material buildup or material erosion on system components in the presence of a plasma. The system components can include, but are not limited to, focus ring 60, shield 14, and electrode plate 24. These exemplary system components are consumable parts, that during plasma processing, commonly become coated, eroded, or both, and therefore require monitoring to facilitate proper replacing.

The role of the focus ring 60 that encircles the substrate 35, includes control of the edge properties in process space 12 above the substrate 35. The status (extent of erosion or material deposition) of focus ring 60 is commonly determined ex-situ by removing the focus ring 60 from the plasma processing system 1 and measuring the reduction or increase in the thickness of the focus ring 60. Alternatively, the status of the focus ring can be evaluated by visual inspection. For example, a change on the order of few tenths of a mm in the thickness of the focus ring 60, can require replacement of the focus ring 60.

During manufacturing of various system components, sensing components containing emitters can be mounted on, in or near system component structures to allow monitoring of component status. In addition, such sensing components need not be manufactured with the system component, but can be provided as a discreet part that is assembled with the system component after manufacturing, at the plasma processing system site, for example. Typical sensing components 28, 32 and 34 are located in or on several internal chamber components previously identified. In addition, sensing component 39 is shown located on the ring shield 62 near the focus ring 60 to determine material buildup or erosion of the ring shield 62 and or focus ring 60. The preferred location of the sensing components can be determined from process history and process requirements. When materials deposit or are eroded from the sensing component, changes in the fluorescent emission can result and can indicate cleaning or replacing of system components.

Various consumable or replaceable components, as well as associated sensing components, of a plasma processing system are, for example, fabricated from silicon, quartz, alumina, carbon, or silicon carbide. Examples of consumable system components that are fabricated from these materials include, electrodes, shields, rings, baffles and liners. The consumable nature of the replaceable components can require frequent maintenance of the plasma processing system. In addition to the above mentioned materials, system components and sensing components can be fabricated from metals (e.g., aluminum) and metal alloys (e.g., stainless steel) and require frequent cleaning or replacing.

Various materials (e.g., quartz and alumina) that are used to manufacture system components and sensing components are substantially transparent to plasma light over a wide range of wavelengths. Fluorescent emission can be observed from emitters associated with the sensing components, even if the emitters are not in direct contact (e.g., encapsulated by the sensing component material) with the plasma environment. Thus, an emitter may be "exposed to a plasma" and thereby emit light without being in direct contact with the plasma. The amount of material deposited on or eroded from a sensing component can be determined when the fluorescent light emission changes.

Monitoring material deposition or erosion on a sensing component using an optical monitoring system can include determining if the intensity level of the fluorescent emission has changed beyond acceptable limits, thus arriving at a determination of whether the system component associated with the sensing component needs to be cleaned or replaced, and based on the determination, either continuing with the process or stopping the process.

When emitters in the sensing component are excited by the plasma, plasma light is absorbed and subsequently re-emitted as fluorescent light that is shifted to longer wavelengths than the absorbed plasma light. The absorbed plasma light can be in the visible region. The shift to longer wavelengths can be advantageous, since light in the visible region is less affected by contaminants, such as polymers and by-products, that can deposit on the optical window 17 of the optical monitoring system 21 during processing. Exposure of the emitters to energetic species other than light in the plasma (e.g., excited gas species) can also result in fluorescent light emission.

Emitters associated with sensing components can be selected from a wide variety of materials (e.g., fluorescent materials, that are commercially available in the form of rigid or non-rigid sheets, fine powders, or paints, for example). The emitters can be encapsulated within sensing components, formed as layers within the sensing component, or placed on outer surfaces of these components. The sensing components can be partially or fully coated by the fluorescent emitter materials. The emitters can contain at least one material having fluorescent properties corresponding to a light wavelength produced in plasma. The fluorescent materials can be selected in view of the desired fluorescent properties, which can depend on the plasma species, and the plasma chemistry within the plasma processing system. The selection of a fluorescent material may be evaluated in view of possible contamination of the process environment, due to exposure of fluorescent material to the plasma, and possible erosion of fluorescent material from a sensing component.

Phosphorus compounds are examples of fluorescent materials that are frequently used in display applications. Phosphors are capable of emitting light in the visible and/or ultraviolet spectrums upon excitation of the material by an external energy source such as plasma. Phosphor powders can have well controlled color characteristics sometimes referred to as emission spectrum characteristics or chromacity. Phosphors typically include a matrix compound, referred to as a host material, and one or more dopants, referred to as activator ions, to emit a specific color or to enhance the luminescence characteristics. The phosphor materials (the color of the fluorescent light in parentheses), can include $Y_2O_3$:Eu (red), $Y_2O_2S$:Eu (green), ZnS:Cu, Al or combinations thereof (green), $SrGaS_4$:Ce (blue), ZnS:Ag, Au or Cl or combinations thereof (blue) and $SrGa_2S_4$:Ce (blue). In addition, $Y_2O_2S$:Tb or $Y_2O_2S$:EuTb may be included in the emitter. The above-identified phosphors are exemplary; a wide variety of other phosphors can be utilized.

Figure 2A:
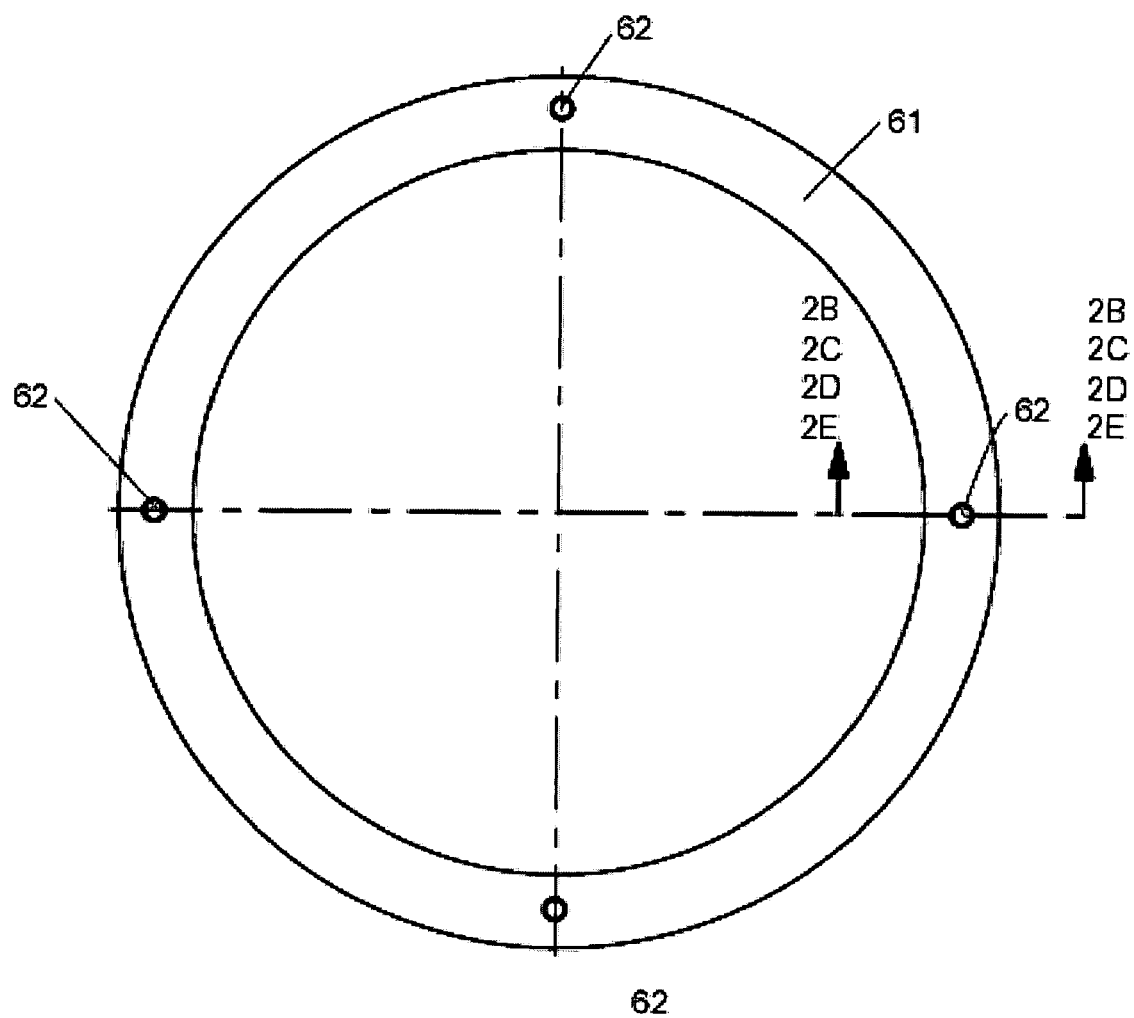
FIG. 2A shows a plan view of a sensing component added to system component.

FIG. 2A shows a plan view of a system component containing a plurality of discreet sensing components 62 attached to the system component 61. The sensing component may be various configurations as long as it includes a main body for containing emitter material and some mating feature that enables the sensing component to be mated to a receiving feature in an object in the processing system such as the component to be sensed. The mating feature of the sensing component may be as simple as a planar surface that is bonded to a planar surface (i.e. receiving feature) of the object in the plasma processing system. More complex configurations of the sensing compound will be described with respect to FIG. 2 through FIG. 11 below.

In the exemplary embodiment shown in FIG. 2A, the system component is a ring 61. The ring 61 can, for example, be a focus ring, an insulator ring, or a shield ring. Emitters, capable of emitting fluorescent light when exposed to a process plasma, are integrated into the sensing component 62 and are therefore attached to the system component 61. The number of sensing components 62 shown in FIG. 2A is exemplary; any number of sensing components can be utilized. The emitters in the sensing components 62 contain at least one fluorescent material. The sensing components 62 can contain different fluorescent materials, or alternatively, the sensing components 62 can contain the same fluorescent material(s). Although the sensing components 62 are shown as round in shape in the embodiment in FIG. 2A, this is not required for the invention. In alternate embodiments, the sensing components 62 can have different shapes including non-geometrical and geometrical shapes, such as, for example, rectangular, square, elliptical and triangular shapes. Relative locations of the sensing components 62 with respect to the ring 61 are exemplary; any number of locations of sensing components 62 can be utilized.

Figure 2B:
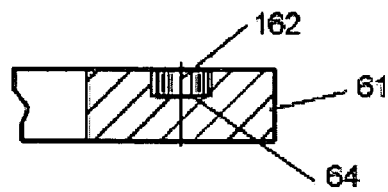
FIG. 2B shows a cross-sectional view of the sensing component and system component in FIG. 2A.

FIG. 2B shows a cross-sectional view of a sensing component mated with the system component in FIG. 2A in accordance with one embodiment of the invention. As seen in the figure, a main body of the sensing component is a disk shaped body, which includes emitter material. The ring 61 is configured with a counterbore feature 64 that functions as a receiving feature to the periphery of the sensing component 162, to thereby retain the sensing component 162 in place in the ring 61. In a preferred embodiment, the sensing component 162 is made of a predetermined size to fits snugly within the counter bore feature so as to aid in retaining the sensing component 162. Thus, the peripheral shape and/or size of the sensing component may function as the mating feature for mating the sensing component 162 to an object such as the ring 61. Any suitable bonding material for use in a semiconductor processing environment may be used to mate the sensing component to the ring 61.

Figure 2C:
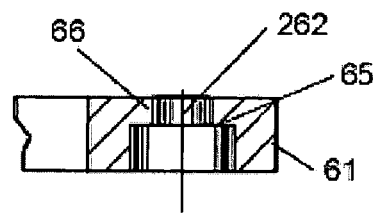
FIG. 2C shows a cross-sectional view of another embodiment of the sensing component and system component in FIG. 2A.

FIG. 2C shows a cross-sectional view of a sensing component mated to the system component in FIG. 2A in accordance with an embodiment of the invention. The ring 61 is configured with a counterbore feature 65 and a thru hole feature 66 that function as receiving features to receive corresponding mating features of the sensing component 262, to retain the sensing component 262 in place in the ring 61. Thus, the mating feature of the sensing component may be a multi feature configuration that is contoured or "keyed" to mate with a similarly shaped receiving feature in an object such as the ring 61. A main body of the sensing component 262 is preferably the portion of the sensing component in the through hole 66, but the portion in counterbore 65 may also include emitter material.

Figure 2D:
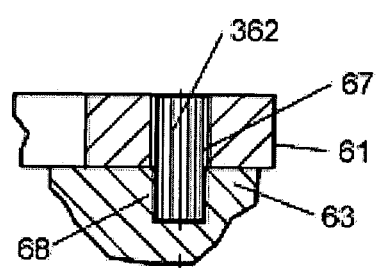
FIG. 2D shows a cross-sectional view of another embodiment of the sensing component and system component in FIG. 2A.

FIG. 2D shows a cross-sectional view of a sensing component mated to the system component in FIG. 2A in accordance with one embodiment of the invention. An underlying structure 63 of the ring 61 is configured with a receiving feature 68, which supports and locates the sensing component 362 with respect to the ring 61. The ring 61 is configured with a thru hole feature 67 as shown. Thus, the receiving feature may include an underlying structure adjacent to the object to which the sensing component is attached (such as the ring 61). Where the sensing component is attached to a focus ring such as the ring 60 in FIG. 1, the underlying structure may be the substrate holder 30 of FIG. 1. Moreover, as used herein, the term "mated" does not necessarily mean that the sensing component is physically fixed to an object. For example, the sensing component 362 may be held in a fixed position with respect to the ring 61 by the structure 63; however, the sensing component may or may not be physically attached to the ring 61 by snug fit or another suitable bonding mechanism. In the embodiment of FIG. 2D, the main body containing the emitter material is preferably that portion of the sensing component in the through hole 67. However, the portion of the sensing component 362 within the receiving feature 68 may also include emitter material.

Figure 2E:
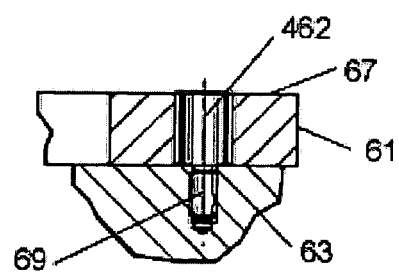
FIG. 2E shows a cross-sectional view of another embodiment of the sensing component and system component in FIG. 2A.

FIG. 2E shows a cross-sectional view of the sensing component attached to the system component in FIG. 2A in accordance with one embodiment of the invention. As seen in FIG. 2A, the underlying structure 63 of the ring 61 is configured with a threaded receiving feature 69, which supports and locates the sensing component 462 with respect to the ring 61. The ring 61 is configured with a thru hole feature 67 as shown.

The embodiments shown in FIG. 2B, FIG. 2C, FIG. 2D and FIG. 2E are exemplary; alternate shapes and configurations for sensing components and associated mating configurations can be utilized. For example, while FIGS. 2B–2E show the sensing component recessed within a ring 61, it is to be understood that any portion or all of the sensing component may protrude from a surface of the object that the sensing component is attached to.

Figure 3A:
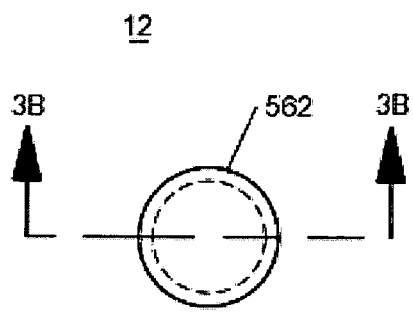
FIG. 3A shows a plan view of a sensing component containing a sensing component and an associated fluorescent emitter.

FIG. 3A shows a plan view of a typical sensing component 562 located somewhere within process space 12. An emitter 563, capable of emitting fluorescent light when exposed to plasma, is integrated into the sensing component 562. Although the emitter 563, is shown as round in the embodiment in FIG. 3A, this is not required for the invention. In alternate embodiments, the emitters can have different shapes including non-geometrical and/or geometrical shapes, such as rectangular, circular, elliptical and triangular shapes. FIG. 3B shows a cross-sectional view of the sensing component in FIG. 3A. Although the cross-sectioned shape of the emitter 563 is shown as a rectangle in the embodiment in FIG. 3B, this is not required for the invention. In alternate embodiments, the emitter's cross-section can have different shapes including non-geometrical and/or geometrical shapes as discussed above with respect to FIG. 3A. The emitter 563 can be fully encapsulated by the sensing component material (e.g., quartz, alumina or silicon) such that the cover portion 527 over the emitter 563 is made of the same material as the rest of the surrounding material 529 of the sensing component 562. Alternately, the emitter 563 can be partially encapsulated within the surrounding material 529 but covered by a portion 527 of a different material. As such, the cover portion 527 can be made of either transparent material or an opaque material. The cover portion 527 can even be made of a filtering material such that a limited number of wavelengths are passed to and from the emitter 563.

Figure 3C:
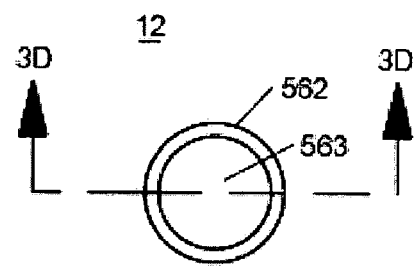
FIG. 3C shows a plan view of the eroded sensing component of FIG. 3A.
Figure 3B:
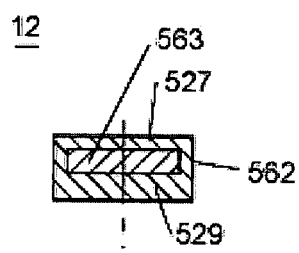
FIG. 3B shows a cross-sectional view of the sensing component in FIG. 3A.
Figure 3D:
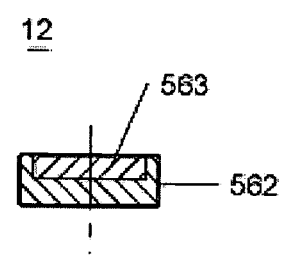
FIG. 3D shows a cross-sectional view of the eroded sensing component in FIG. 3C.

FIG. 3C shows a plan view of an eroded sensing component 562 containing an emitter 563. Exposure of the sensing component 562 to plasma can result in erosion of the sensing component 562 and direct exposure to the emitter 563. Optical monitoring of the process space 12, and the onset of or a significant increase in characteristic fluorescent light emission from the emitter 563, can be utilized to determine whether the system component associated with the sensing component or components needs to be replaced. FIG. 3D shows a cross-sectional view of the sensing component in FIG. 3C. While FIGS. 3A–3D show a sensing component having a disk shape that may serve as a mating feature for a corresponding receiving feature of an object, other mating features may be utilized with the sensing component 562.

Figure 4E:
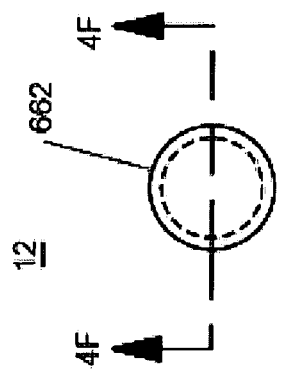
FIG. 4E shows a plan view of a sensing component containing a fluorescent emitter with a layer of deposited material.
Figure 4F:
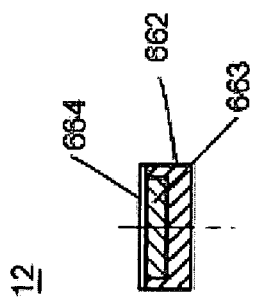
FIG. 4F shows a cross-sectional view of the sensing component of FIG. 4E with a layer of deposited material.

Alternatively, emitters can be integrated into sensing components so that emitters are partially encapsulated by sensing component material (e.g., quartz, alumina, or silicon). FIG. 4A shows a plan view of a sensing component 662 containing a partially encapsulated emitter 663. FIG. 4B shows a cross-sectional view of the sensing component 662 in FIG. 4A.

Figure 4C:
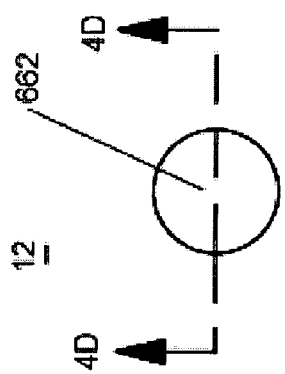
FIG. 4C shows a plan view of an eroded sensing component with a completely eroded fluorescent emitter.
Figure 4D:
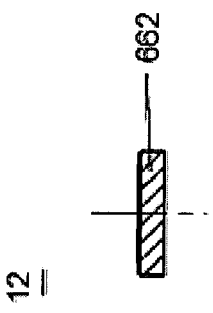
FIG. 4D shows a cross-sectional view of an eroded sensing component in FIG. 4C.
Figure 4A:
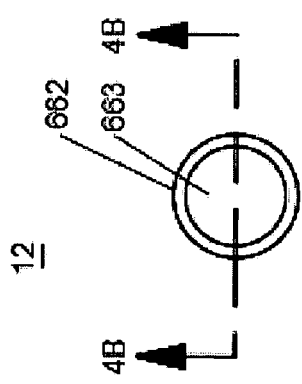
FIG. 4A shows a plan view of a sensing component containing a fluorescent emitter.
Figure 4B:
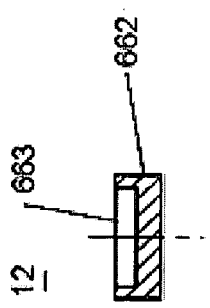
FIG. 4B shows a cross-sectional view of the sensing component in FIG. 4A.

FIG. 4C shows a plan view of an eroded sensing component. Exposure of the sensing component 662 to plasma in the process space 12 can result in erosion of the sensing component 662 and the emitter 663. Optical monitoring of the plasma processing system, and the disappearance of or a significant decrease in the characteristic fluorescent light emission can be utilized to determine whether the system component, associated with the sensing component or components needs to be replaced. FIG. 4D shows a cross-sectional view of the eroded sensing component in FIG. 4C.

FIG. 4E shows a plan view of a sensing component 662 located in a process space 12, containing a fluorescent emitter 663 with a layer of deposited material 664. FIG. 4F shows a cross-sectional view of the sensing component 662, emitter 663 and deposited layer 664. The deposited layer 664 can, for example, consist of polymer deposits from plasma etching processes. Optical monitoring of the process space 12, and disappearance of or a significant decrease in characteristic fluorescent light emission from the emitter 663 below a threshold value, can be utilized to determine whether the system components associated with the sensing component or components needs to be cleaned or replaced. While FIGS. 4A–4F show a sensing component having a disk shape that may serve as a mating feature for a corresponding receiving feature of an object, other mating features may be utilized with the sensing component 662.

Figure 5C:
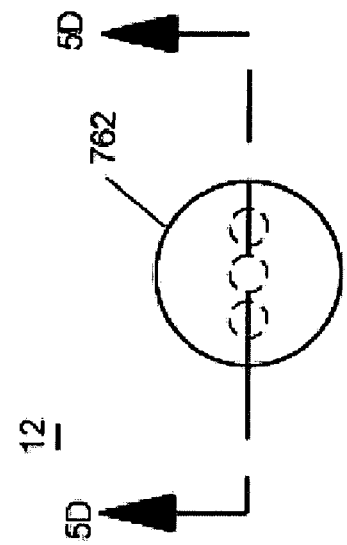
FIG. 5C shows a plan view of the eroded sensing component in FIG. 5A.
Figure 5D:
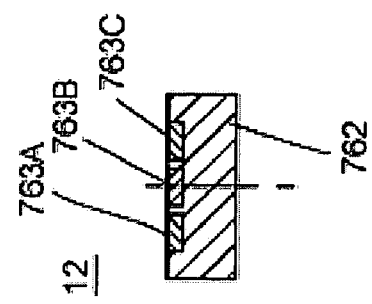
FIG. 5D shows a cross-sectional view of the sensing component of FIG. 5C.
Figure 5A:
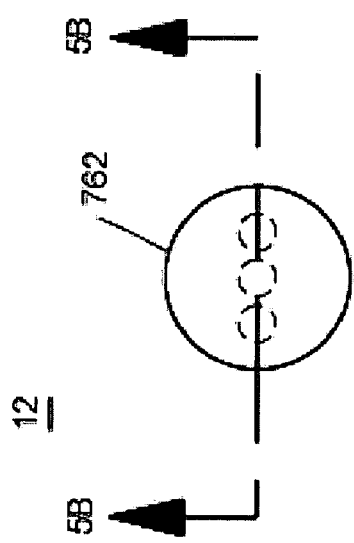
FIG. 5A shows a plan view of a sensing component containing a plurality of fluorescent emitters.
Figure 5B:
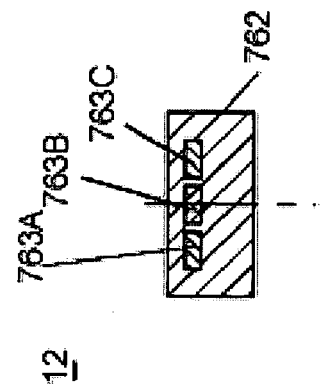
FIG. 5B shows a cross-sectional view of the sensing component in FIG. 5A.

FIG. 5A shows a plan view of a sensing component 762 containing a plurality of emitters 763A, 763B and 763C. Emitters 763A, 763B and 763C, capable of emitting fluorescent light when exposed to a plasma, in a process space 12, are integrated to the sensing component 762 at different positions and are fully encapsulated by the sensing component material. The number of emitters is exemplary; any number of emitters can be utilized. The emitters 763A, 763B and 763C can contain different fluorescent materials, or alternately, the emitters can contain the same fluorescent material(s). By using one set of materials at one location and by using a different set of materials at other locations, the optical emissions of the sensing component 762 can be spatially resolved. FIG. 5B shows a cross-sectional view of the sensing component 763 in FIG. 5A.

FIG. 5C shows a plan view of an eroded sensing component 762. Exposure of the sensing component 762 to a plasma in the process space 12, can result in the erosion of the sensing component 762 and direct exposure of one or more of the emitters 763A, 763B and 763C to the plasma. Optical monitoring of the plasma processing system, and the onset of or significant increase in characteristic fluorescent light emission can be utilized to determine whether the system component associated with the sensing component or components needs to be replaced. FIG. 5D shows a cross-sectional view of the eroded system component in FIG. 5C. If the sensing component 762 erodes uniformly, fluorescent light emissions from the emitters 763A, 763B and 763C can appear substantially at the same time. However, if the sensing component etches non-uniformly (not shown) during plasma processing, the characteristic fluorescent light emission from one or more of the emitters 763A, 763B and 763C can provide spatial erosion information, in addition to the extent of the erosion. While FIGS. 5A–5D show a sensing component having a disk shape that may serve as a mating feature for a corresponding receiving feature of an object, other mating features may be utilized with the sensing component 762.

Figure 6A:
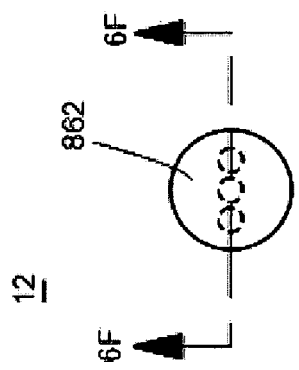
FIG. 6A shows a plan view of a sensing component containing a plurality of fluorescent emitters.

Alternatively, emitters can be integrated into sensing components so that emitters are partially encapsulated by sensing component material (e.g., quartz, alumina, or silicon). FIG. 6A shows a plan view of a sensing component 862 containing emitters 863A, 863B and 863C. FIG. 6B shows a cross-sectional view of the sensing component 862 in FIG. 6A.

Figure 6C:
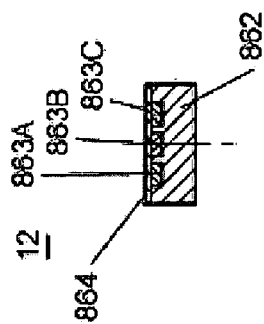
FIG. 6C shows a plan view of the eroded sensing component in FIG. 6A.

FIG. 6C shows a plan view of an eroded sensing component. Exposure of the sensing component 862 to plasma in the process space 12 can result in erosion of the sensing component 862 and the emitters 863A, 863B and 863C. Optical monitoring of the plasma processing system, and the disappearance of or a significant decrease in the characteristic fluorescent light emission can be utilized to determine whether the system component, associated with the sensing component or components needs to be replaced. FIG. 6D shows a cross-sectional view of the sensing component in FIG. 6C.

Figure 6E:
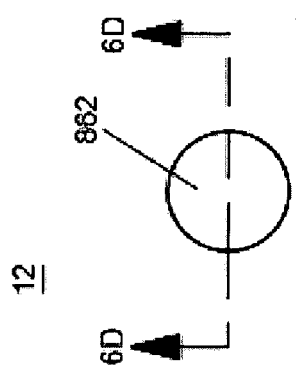
FIG. 6E shows a plan view of a sensing component containing a plurality of fluorescent emitters with a layer of deposited material.
Figure 6B:
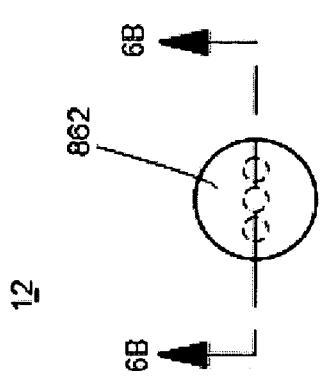
FIG. 6B shows a cross-sectional view of the sensing component in FIG. 6A.
Figure 6D:
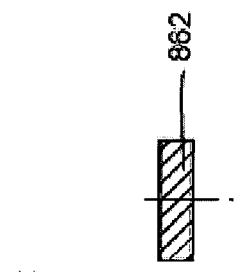
FIG. 6D shows a cross-sectional view of an eroded sensing component in FIG. C.
Figure 6F:
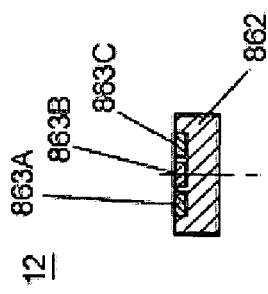
FIG. 6F shows a cross-sectional view of a sensing component of FIG. 6E with a layer of deposited material.

FIG. 6E shows a plan view of a sensing component 862 located in a process space 12, containing a fluorescent emitters 863A, 863B and 863C with a layer of deposited material 864. FIG. 6F shows a cross-sectional view of the sensing component 862, emitters 863A, 863B, 863C and deposited layer 864. The deposited layer 864 can, for example, consist of polymer deposits from plasma etching processes. Optical monitoring of the process space 12, and disappearance of or a significant decrease in characteristic fluorescent light emission from the emitters 863A, 863B and 863C below a threshold value, can be utilized to determine whether the system components associated with the sensing component or components needs to be cleaned or replaced. While FIGS. 6A–6F show a sensing component having a disk shape that may serve as a mating feature for a corresponding receiving feature of an object, other mating features may be utilized with the sensing component 862.

Figure 7A:
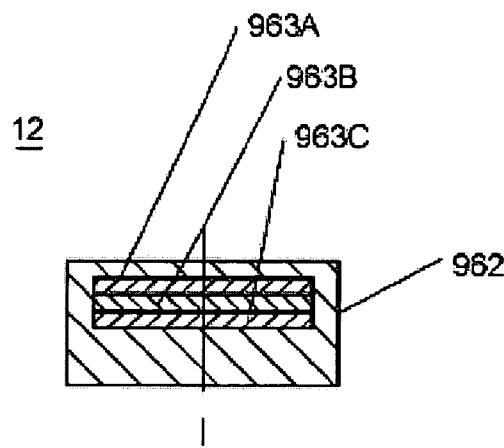
FIG. 7A shows a cross-sectional view of a sensing component containing a plurality of fluorescent emitters.

FIG. 7A shows a cross-sectional view of a sensing component 962 containing an emitter stack including layers 963A, 963B and 963C. In the first embodiment of the stack, the layers 963A, 963B and 963C are each a different type of fluorescent material such that the erosion of each layer is signaled by a change to a new emission type. In the second embodiment, the first layer 963A is an opaque layer that initially blocks transmission of light to the third layer 963C which is made from a fluorescent material. In the second embodiment, the second layer 963B can be either a (substantially) transparent layer or a filter. If the second layer 963B reduces the amount of emission by the third layer 963C, then the erosion of the second layer 963B will be signaled by an increasing amount of emission from the third layer 963C.

Figure 7B:
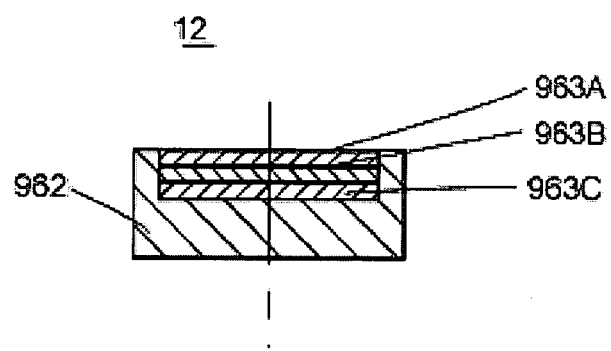
FIG. 7B shows a cross-sectional view of an eroded sensing component of FIG. 7A.

FIG. 7B shows a cross-sectional view of an eroded sensing component 962 containing layers 963A, 963B and 963C of fluorescent materials. Exposure to the plasma in the processing space 12 can result in erosion of the sensing component and direct exposure of layer 963A to the plasma. In the first embodiment described above, optical monitoring of the plasma processing system, and the onset of or significant increase in characteristic fluorescent light emission from the layer 963A can be utilized to determine the status of the system component by associating with its sensing component(s). In addition, disappearance of a characteristic fluorescent light emission from an emitter can be used to determine the status of a system component via usage of a sensing component(s).

Figure 7C:
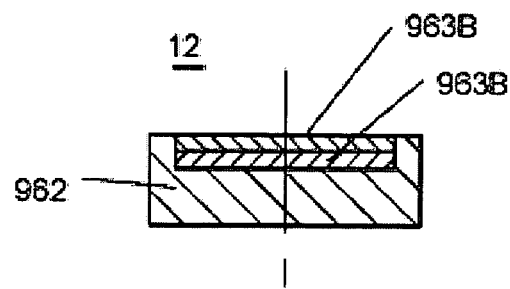
FIG. 7C shows a cross-sectional view of an eroded sensing component of FIG. 7B.

FIG. 7C shows a cross-sectional view of an eroded sensing component 962 containing an emitter stack. Further exposure of the sensing component to the plasma, can result in direct exposure of layer 963B to the plasma. Optical monitoring of the plasma processing system, and the onset of or significant increase in characteristic fluorescent light emission from layer 963B (in the first embodiment) or layer 963C (in the second embodiment) can be utilized to determine the status of a system component by use of one or more sensing components.

Figure 8A:
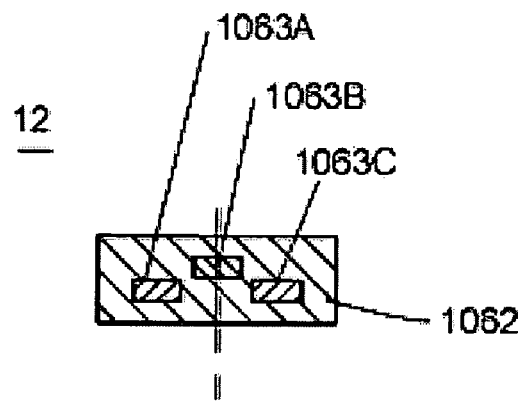
FIG. 8A shows a cross-sectional view of a sensing component containing a plurality of fluorescent emitters.

FIG. 8A shows a cross-sectional view of a sensing component 1062 containing a plurality of emitters 1063A, 1063B and 1063C which are fully encapsulated by the sensing component material. While illustrated as being embedded at different depths, the emitters 1063A, 1063B and 1063C could be embedded at the same depth. As would be appreciated, the depth of each emitter to be buried within the surface may be determined empirically by examining eroded surfaces and when such erosion decreased system performance or cleanliness.

Figure 8B:
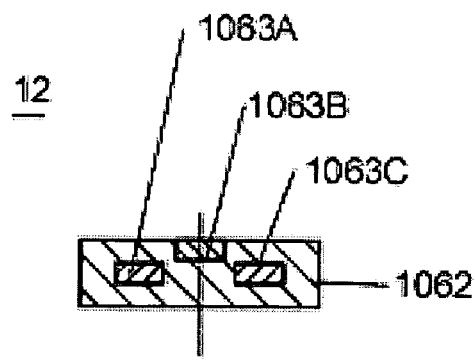
FIG. 8B shows a cross-sectional view of an eroded sensing component of FIG. 8A.
Figure 8C:
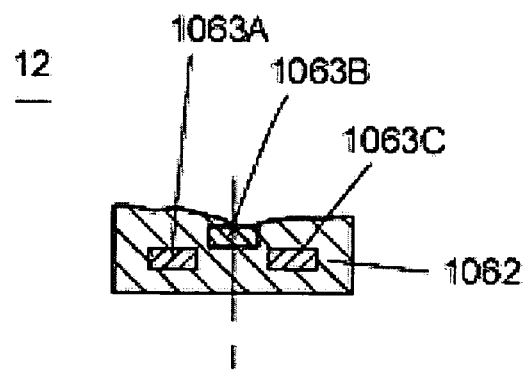
FIG. 8C shows a cross-sectional view of an eroded sensing component of FIG. 8A.

FIG. 8B shows a cross-sectional view of an eroded sensing component 1062 containing a plurality of emitters. The sensing component 1062 is uniformly eroded, and fluorescent signals from emitters 1063A, 1063B and 1063C can appear substantially at the same time. FIG. 8C shows a cross-sectional view of an eroded sensing component containing a plurality of emitters. If the sensing component etches non-uniformly during plasma processing, the characteristic fluorescent light emission from one or more emitters 1063A, 1063B and 1063C can provide spatial erosion information, in addition to information on the extent of the erosion.

Figure 9A:
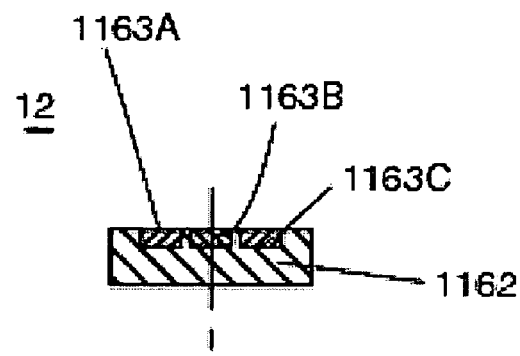
FIG. 9A shows a cross-sectional view of a sensing component containing a plurality of fluorescent emitters.

FIG. 9A shows a cross-sectional view of a sensing component 1162 containing a plurality of emitters 1163A, 1163B and 1163C. In FIG. 9A, the emitters 1163A, 1163B and 1163C are partially encapsulated by the ring material.

Figure 9B:
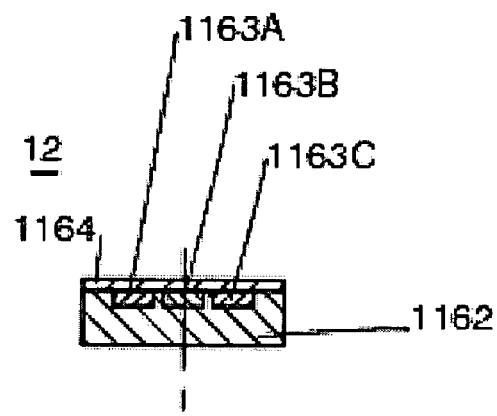
FIG. 9B shows a cross-sectional view of the sensing component of FIG. 9A with a layer of deposited material.
Figure 9C:
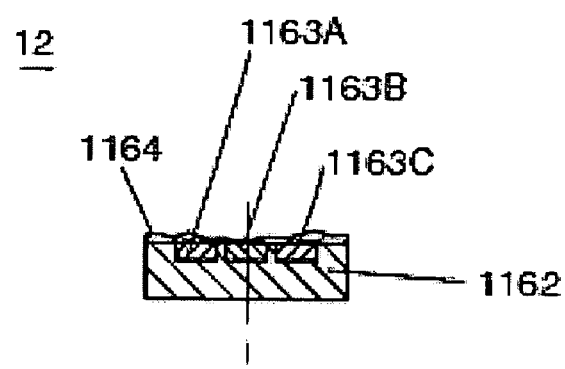
FIG. 9C shows a cross-sectional view of the sensing component of FIG. 9A with a layer of deposited material.

FIG. 9B shows a cross-sectional view of the sensing component in FIG. 9A with a layer of deposited material 1164. The sensing component is uniformly coated, and fluorescent signals from emitters 1163A, 1163B and 1163C can appear substantially at the same time. FIG. 9C shows a cross-sectional view of the sensing component 1162 that is non-uniformly coated by layer 1164 and the characteristic fluorescent light emission from one or more emitters can provide spatial deposition information, in addition to information on the extent of the deposition on the sensing component.

Different system components in a plasma processing system can be associated with different sensing components that contain different fluorescent materials that allow identifying and monitoring a particular system component. In addition, a single system component can be associated with sensing components with different fluorescent materials at different spatial locations to allow monitoring of material removal or buildup on these sensing components which then relates to removal or buildup on system components. Sensing components can contain protective barriers that are deposited on the surfaces of the sensing components, similar to barriers applied to system components. The role of the protective barrier can be to reduce erosion of the sensing component during plasma processing. A protective barrier comprising, for example Yttria ($Y_2O_3$), can be formed using (thermal) spray coating techniques that are well known to those skilled in the art of ceramic spray coatings. In an alternate embodiment, forming the protective barrier can further comprise polishing the thermal spray coating. For example, polishing the thermal spray coating can comprise the application of sand paper to sprayed surfaces. The protective barrier can comprise at least one of $Y_2O_3$, $Sc_2O_3$, $Sc_2F_3$, $YF_3$, $La_2O_3$, $Ce_3O_2$, $Eu_2O_3$, $DyO_3$, $SiO_2$, $MgO$, $Al_2O_3$, $ZnO$, $SnO_2$ and $In_2O_3$. The protective barrier thickness can range from 0.5 microns to 500 microns, for example. Alternately, the protective barrier can compromise a phosphor material, e.g., $Y_2O_3$:Eu. Disappearance or some change of a characteristic fluorescent light emission from a phosphor material in a protective barrier can be used to determine status of a sensing component and hence the status of an associated system component.

Figure 10A:
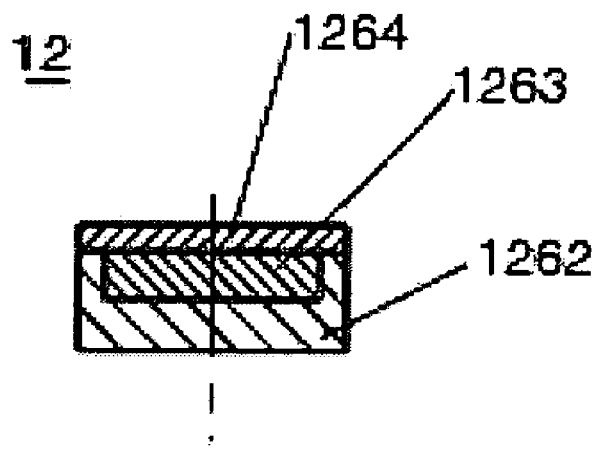
FIG. 10A shows a cross-sectional view of a sensing component containing a fluorescent emitter and a protective layer.
Figure 10B:
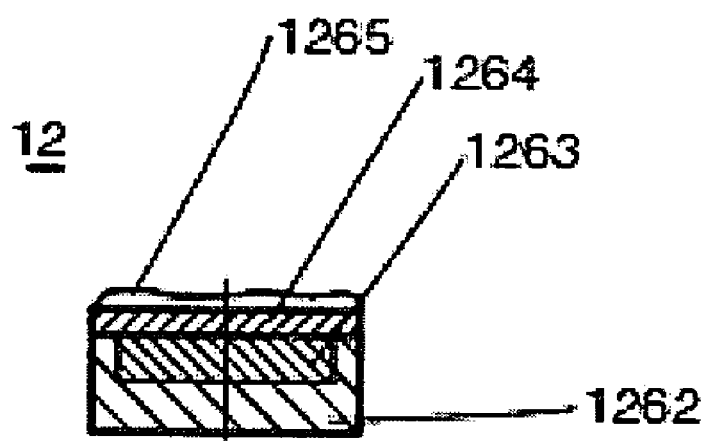
FIG. 10B shows a cross-sectional view of the sensing component of FIG. 10A with a layer of deposited material.

FIG. 10A and FIG. 10B show cross-sectional views of a sensing component 1262 containing an emitter 1263. FIG. 10A shows a protective barrier 1264 deposited on the emitter 1263 and sensing component 1262. FIG. 10B shows a layer 1265 deposited on the sensing component 1262. Changes in the fluorescent emissions from the emitter 1263 during plasma processing, in the process space 12, can indicate status changes on the protective barrier 1264.

Figure 11A:
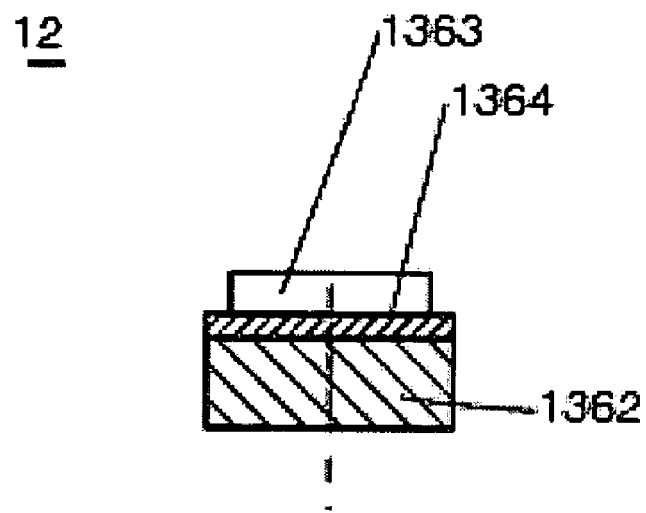
FIG. 11A shows a cross-sectional view of a sensing component containing a fluorescent emitter and a protective layer.
Figure 11B:
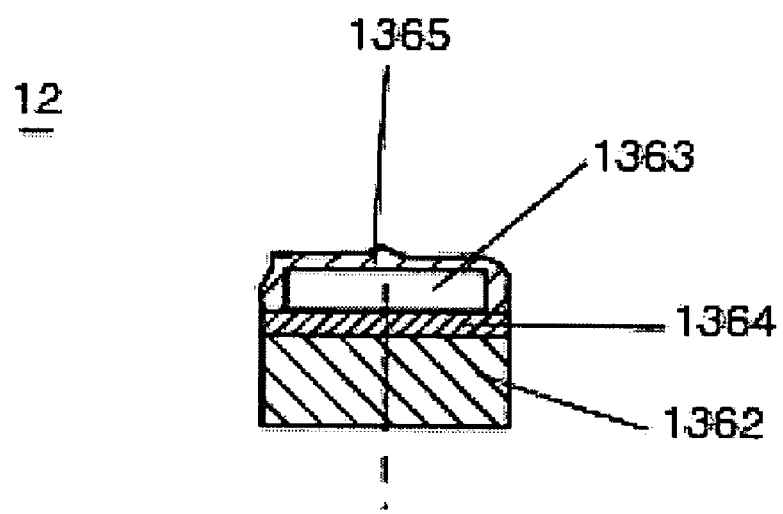
FIG. 11B shows a cross-sectional view of the sensing component of FIG. 10A with a layer of deposited material.

FIG. 11A and FIG. 11B show a cross-sectional view of a sensing component 1362 containing an emitter 1363. FIG. 11A shows an emitter 1363 overlying a protective barrier layer 1364 deposited on the sensing component 1362. Changes in the fluorescent emissions from the emitter 1363 during plasma processing, in process space 12, can indicate deposition 1365 on the emitter layer 1363 and thus deposition on the system component associated with the sensing component. While FIGS. 7–11 show a sensing component having a disk shape that may serve as a mating feature for a corresponding receiving feature of an object, other mating features may be utilized with the sensing component of these figures. Moreover, in one embodiment of the invention (not shown), a transparent or translucent material can be provided over the emitter material to protect the emitter from damage (e.g., cause by exposure to plasma). Such a material may either pass all wavelengths or may filter out a subset of the light from the plasma and/or from the emitter located within the sensing component.

The status of a system component can be determined during plasma processing, by monitoring the characteristic fluorescent emission from an emitter integrated to a sensing component that is associated with the system component. One possible method for determining the status of sensing components and related system components is to use optical emission spectroscopy (OES) to monitor a wavelength range where the characteristic fluorescent emission occurs. A sensing component can contain at least one emitter, that is capable of fluorescent emission at characteristic wavelength (s), that allow for identification of the system component. When an intensity level of an emission with a characteristic wavelength crosses a specified threshold value (e.g., increase above a particular value or drop to substantially zero), a determination can be made whether the sensing component and therefore the system component needs to be cleaned or replaced, and based on that determination, the process can be continued or stopped.

Figure 12:
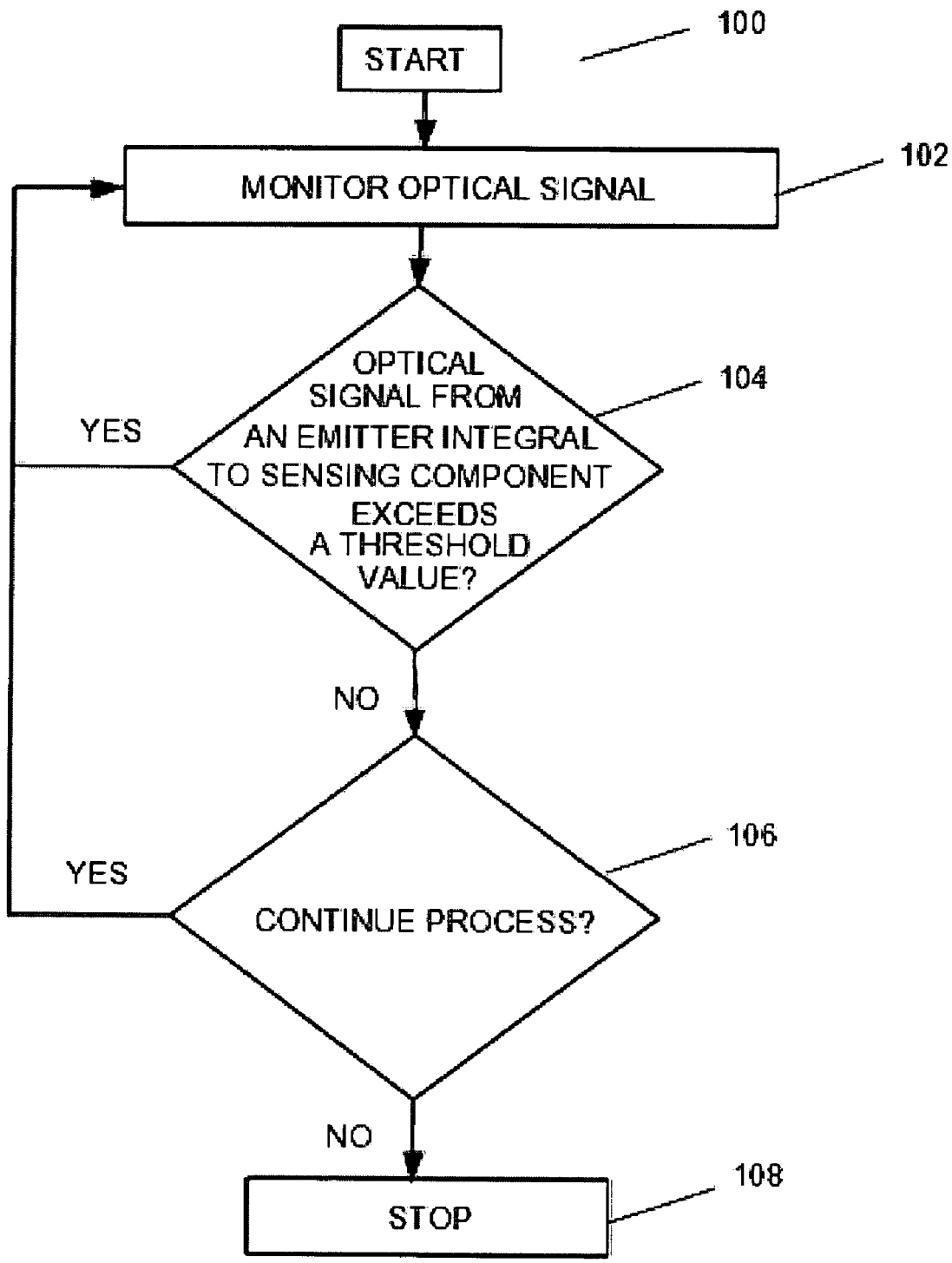
FIG. 12 is a flowchart for monitoring the status of system components using optical emission.

FIG. 12 is a flowchart for monitoring the status of system components via sensing components using optical emission. In step 100, the process is started. In step 102, an optical signal from the plasma processing reigon is monitored using an optical monitoring system. In step 104, the optical signal is analyzed for characteristic light emission from an emitter integrated into a sensing component that is associated with a system component. If the characteristic light emission from an emitter falls outside set values, a determination is made in step 106 on whether to continue the process or to stop the process in step 108.

Determining whether the process should be continued in step 106 can depend on the fluorescent emission that is detected. Furthermore, fluorescent emission levels from a plurality of sensing components can indicate if a system component is either uniformly coated, or uniformly eroded during plasma processing and therefore can provide spatial deposition or spatial erosion information respectively. Extents of deposition or erosion can be monitored as well.

When the monitoring process of FIG. 12 results in a determination that a semiconductor processing system component needs to be replaced, the processing component may be replaced with a processing component having a sensing component already mated thereto, or may be replaced with a standard processing component that is retrofitted with a sensing component in accordance with the present invention. When a standard processing component is retrofitted with a sensing component, a receiving feature is first formed in the standard component for receiving the sensing component. Forming the receiving feature on the processing component may be applying a suitable adhesive to the surface of the processing component in an area to which the sensing component will be mated with the surface of the processing component. Alternatively, preparing a receiving feature in the processing component may include machining such as drilling, boring, or forming a threaded hole in the processing component at a location where the sensing component is to be mated with the processing component.

Once the receiving feature is formed in the processing component, a mating feature of the sensing component is then mated with the receiving feature in the processing component. The processing component having the sensing component mated thereto is then placed in the semiconductor processing chamber.

In an alternative embodiment, the sensing component may be inserted into a receiving feature already formed in an object within the processing chamber that is not being replaced. For example, where the sensing component is placed on an object that does not erode in order to sense the erosion of a processing component adjacent to the object, the plasma that erodes the component may erode and/or damage the sensing feature to the extent that the sensing feature needs to be replaced after one or more replacements of the processing component. Alternatively, the sensing component may be placed on or adjacent to a system component to be sensed may become damaged during a chamber cleaning process, for example. In these situations, a sensing component having an appropriate mating feature is simply mated with a receiving feature of the object within the semiconductor processing chamber. In this regard, a damaged or eroded sensing component will typically have to be removed from the receiving feature before the new sensing component is mated thereto. However, in some situations, the sensing component is made of such a material that the entire sensing component will be eroded by a process environment in the semiconductor processing chamber, thereby obviating the need to remove a damaged or eroded sensing component.

This method of monitoring the status of system components using sensing components with integral emitters, provides a new in-situ method for monitoring material buildup and erosion of system components in a plasma environment. The deposition of material onto consumable system components and the erosion of consumable system components can be monitored during plasma processing, without the need for disassembly of the plasma processing system. The method can significantly reduce the risk of overdue or premature replacement of consumable components, and avoid processing conditions that are outside process specifications due to deposition of materials onto system components. Moreover, the use of discreet sensing components enables the components to be mass produced separately from the system component to be sensed. This provides inexpensive manufacturing of the sensor components, and enables retrofitting of standard system components, and/or the system chamber itself, with the sensing component. That is, a semiconductor processing chamber that is incapable of in-situ monitoring of erosion or material buildup on internal chamber parts can be easily retrofitted for such monitoring by installing a sensor component of the present invention and utilizing standard optical monitoring equipment to monitor the light emission of the sensor component.

It should be understood that modifications and variations of the present invention may be employed in practicing the invention. It is therefore to be understood that, within the scope of the appended claims, the invention may be practiced otherwise than specifically described herein.

The invention claimed is:

1. A sensing device for sensing a condition of a plasma processing system component, comprising:
 a main body configured to contain a material;
 an emitter contained in said main body and configured to emit light when exposed to a plasma; and
 a mating feature connected to said main body and configured to be mated with a receiving feature of an object in said plasma processing system such that said emitter material is exposed to a processing environment of said plasma processing system, wherein when said emitter material is exposed to a plasma, said light emitted from the emitter can be monitored to determine material accumulation on said system component.

2. The sensing device of claim 1, wherein said main body comprises a predetermined shape configured to provide said mating feature to be mated with a receiving feature of an object in the plasma processing system.

3. The sensing device of claim 1, wherein said emitter is contained in said main body as one of an encapsulated material within the main body, a layered material within the main body, and a painted material on the main body.

4. The sensing device of claim 1, wherein said mating feature comprises a first feature configured to be received by a through hole of said object, and a second feature configured to be received by a counter bore of said object.

5. The sensing device of claim 1, wherein said mating feature comprises a protrusion configured to protrude from said object to a receiving portion of an underlying structure.

6. The sensing device of claim 5, wherein said protrusion comprises a threaded protrusion.

7. The sensing device of claim 1, wherein said main body comprises at least one of silicon, quartz, alumina, carbon, silicon carbide, aluminum, and stainless steel.

8. The sensing device of claim 1, wherein said emitter comprises at least one material having fluorescent properties when excited by a light produced in said plasma.

9. The sensing device of claim 1, wherein said emitter comprises at least one material having fluorescent properties when excited by excited gas species produced in said plasma.

10. The sensing device of claim 9, wherein said at least one material comprises a phosphor material.

11. The sensing device of claim 1, wherein said emitter comprises at least one of $Y_2O_3$:Eu, $Y_2O_2S$:Eu, $Y_2O_2S$:Tb, $Y_2O_2S$:EuTb, ZnS:Al, ZnS:CuAl, $SrGa_2S_4$:Ce, ZnS:Ag, ZnS:Au, ZnS:Cl, ZnS:AgAu, ZnS:AgCl, ZnS:AuCl, ZnS:AgAuCl and $SrGa_2S_4$;Ce.

12. The sensing device of claim 1, further comprising a protective barrier configured to protect said emitter from a process environment of said plasma processing system.

13. The sensing device of claim 12, wherein said protective barrier comprises at least one of $Y_2O_3$, $Sc_2O_3$, $Sc_2F_3$, $YF_3$, $La_2O_3$, $Ce_3O_2$, $Eu_2O_3$, $DyO_3$, $SiO_2$, MgO, $Al_2O_3$, ZnO, $SnO_2$, and $In_2O_3$.

14. A sensing device for sensing a condition of a plasma processing system component, comprising:
 a main body configured to contain a material;
 an emitter contained in said main body and configured to emit light when exposed to a plasma; and
 a mating feature connected to said main body and configured to be mated with a receiving feature of an object in said plasma processing system such that said emitter material is exposed to a processing environment of said plasma processing system, wherein when said emitter material is exposed to a plasma, said light emitted from the emitter can be monitored to determine at least one of material accumulation on said system component and erosion of said system component,
 further comprising a protective barrier configured to protect said emitter from a process environment of said plasma processing system,
 wherein said protective barrier comprises a material transparent to visible light.

15. A plasma processing system, comprising:
 a plasma processing chamber;
 a plasma source coupled to said plasma processing chamber and configured to create a plasma from a process gas;
 a system component coupled to at least one of said plasma processing chamber and said plasma source;

a sensing component mated to an object in said plasma processing chamber and comprising an emitter capable of light emission when exposed to said plasma; and an optical monitoring system coupled to said plasma processing chamber and configured to monitor light emission from said plasma processing chamber during a process in order to monitor material accumulation on system component.

16. The system according to claim 15, wherein said system component comprises at least one of a consumable part, and a replaceable part.

17. The system according to claim 15, wherein said system component comprises at least one of a ring, a shield, an electrode, a baffle, and a liner.

18. The system according to claim 15, wherein said sensing component and said system component are fabricated from at least one of silicon, quartz, alumina, carbon, silicon carbide, aluminum, and stainless steel.

19. The system according to claim 15, wherein said emitter of said sensing component comprises at least one material having fluorescent properties when excited by a light produced in said plasma.

20. The system according to claim 15, wherein said emitter of said sensing component comprises at least one material having fluorescent properties when excited by excited gas species produced in said plasma.

21. The system according to claim 20, wherein said at least one material comprises a phosphor material.

22. The system according to claim 15, wherein said emitter of said sensing component comprises at least one of $Y_2O_3$:Eu, $Y_2O_2$S:Eu, $Y2O_2$S:Th, $Y_2O_2$S:EuTb, ZnS:Al, ZnS:CuAl, $SrGa_2S_4$:Ce, ZnS:Ag, ZnS:Au, ZnS:Cl, ZnS:AgAu, ZnS:AgCl, ZnS:AuCl, ZnS:AgAuCl and $SrGa_2S_4$; Ce.

23. The system according to claim 15, wherein said sensing component further comprises a protective barrier.

24. The system according to claim 23, wherein said protective barrier comprises at least one of $Y_2O_3$, $Sc_2O_3$, $Sc_2F_3$, $YF_3$, $La_2O_3$, $Ce_3O_2$, $Eu_2O_3$, $DyO_3$, $SiO_2$, MgO, $Al_2O_3$, ZnO, $SnO_2$, and $In_2O_3$.

25. The system according to claim 15, wherein said plasma source comprises an inductive coil.

26. The system according to claim 15, wherein said plasma source comprises a plate electrode.

27. The system according to claim 15, wherein said plasma source comprises an ECR source.

28. The system according to claim 15, wherein said plasma source comprises a Helicon wave source.

29. The system according to claim 15, wherein said plasma source comprises a surface wave source.

30. The system according to claim 15, wherein said optical monitoring system is further configured to measure at least one of a wavelength and a light intensity associated with said light emission.

31. The system according to claim 30, wherein said optical monitoring system is further configured to identify said system component from said wavelength of said light emission.

32. The system according to claim 30, wherein said optical monitoring system is further configured to determine whether said system component requires replacement based on said light intensity.

33. The system according to claim 32, wherein said optical monitoring system is further configured to perform at least one of continuing said process and terminating said process based upon said determination.

34. The system according to claim 15, wherein said system component comprises a plurality of sensing components.

35. A plasma processing system, comprising:
a plasma processing chamber;
a plasma source coupled to said plasma processing chamber and configured to create a plasma from a process gas;
a system component coupled to at least one of said plasma processing chamber and said plasma source;
a sensing component mated to an object in said plasma processing chamber and comprising an emitter capable of light emission when exposed to said plasma; and
an optical monitoring system coupled to said plasma processing chamber and configured to monitor light emission from said plasma processing chamber during a process in order to monitor at least one of material accumulation on and material erosion of said system component,
wherein said sensing component further comprises a protective barrier,
wherein said protective barrier comprises material transparent to visible light.

36. A system component assembly for a plasma processing system comprising:
a system component having a receiving feature and configured to be mounted in a processing environment of said plasma processing system; and
a sensing component having a mating feature coupled to said receiving feature of said system component and comprising an emitter, configured to emit light when exposed to plasma, wherein said light emission is used to monitor a status of at least one of material accumulation on said system component and erosion of said system component.

37. The system component assembly according to claim 36, wherein said system component comprises a ring, an electrode, a baffle, or a liner.

38. The system component assembly according to claim 36, wherein said system component comprises a focus ring.

39. The system component assembly according to claim 36, wherein said system component comprises an electrode plate.

40. The system component assembly according to claim 36, wherein said system component comprises a deposition shield.

41. The system component assembly according to claim 36, wherein said sensing component comprises at least one of silicon, quartz, alumina, carbon, silicon carbide, aluminum and stainless steel.

42. The system component assembly according to claim 36, wherein said emitter is fully encapsulated within said sensing component.

43. The system component assembly according to claim 36, wherein said emitter is partially encapsulated by the sensing component.

44. The system component assembly according to claim 36, wherein said emitter comprises at least one material having fluorescent properties when excited by light produced in plasma.

45. The system component assembly according to claim 36, wherein said emitter comprises at least one material having fluorescent properties when excited by excited gas species produced in said plasma.

46. The system component assembly according to claim 36, wherein said light emission from said emitter allows for identifying said system component.

47. The system component assembly for according to claim 36, wherein said emitter comprises a phosphor material.

48. The system component assembly according to claim 46, wherein said phosphor material comprises at least one of $Y_2O_3$:Eu, $Y_2O_2$S:Eu, $Y_2O_2$S:Tb, $Y_2O_2$S:EuTb, ZnS:Cu, ZnS:Al, ZnS:CuAl, $SrGa_2S4$:Ce, ZnS:Ag, ZnS:Au, ZnS:Cl, ZnS:AgAu, ZnS:AgCl, ZnS:AuCl, ZnS:AgAuCl and $SrGa_2S4$:Ce.

49. The system component assembly according to claim 36, wherein at least one of said sensing component and said system component comprises a protective barrier.

50. The system component assembly according to claim 48, wherein said protective barrier comprises at least one material having fluorescent properties when excited by light produced in said plasma.

51. The system component assembly according to claim 46, wherein said protective barrier comprises at least one material having fluorescent properties when excited by excited gas species produced in said plasma.

52. The system component assembly according to claim 48, wherein the thickness of the protective barrier is less than about 500 microns.

53. A method of configuring a semiconductor processing chamber to enable monitoring of material accumulation on a semiconductor processing part comprising:
obtaining a discreet sensor component containing an emitter configured to emit light of a first intensity when exposed to a plasma and to emit light at a second intensity, different from the first intensity, after material accumulates on the semiconductor processing part; and
mounting said discreet sensor component to at least one of said semiconductor processing part and an object adjacent to said semiconductor processing part.

54. The method of claim 53, wherein said mounting comprises mating said sensor with a recessed receiving feature of said at least one of said semiconductor processing part and an object adjacent to said semiconductor processing part.

55. The method of claim 53, wherein said mounting comprises screwing said sensor component into a receiving feature of said at least one of said semiconductor processing part and an object adjacent to said semiconductor processing part.

56. A method of configuring a semiconductor processing chamber to enable monitoring of at least one of material accumulation on a semiconductor processing part and erosion of the processing part, said method comprising:
obtaining a discreet sensor component containing an emitter configured to emit light when exposed to a plasma; and
mounting said discreet sensor component to at least one of said semiconductor processing part and an object adjacent to said semiconductor processing part, wherein said mounting comprises bonding a mating surface of said discreet sensor component to said at least one of said semiconductor processing part and an object adjacent to said semiconductor processing part using a bonding material.

* * * * *